US008536355B2

(12) United States Patent
Radhakrishnan et al.

(10) Patent No.: US 8,536,355 B2
(45) Date of Patent: Sep. 17, 2013

(54) PROCESS FOR PRODUCING N,N-DIALKYL SUBSTITUTED FATTY ACIDS AMIDES

(76) Inventors: Ramachandran Radhakrishnan, Bangalore (IN); Sisir K. Adhikari, Mumbai (IN)

( * ) Notice: Subject to any disclaimer, the term of this patent is extended or adjusted under 35 U.S.C. 154(b) by 1128 days.

(21) Appl. No.: 11/575,959

(22) PCT Filed: Sep. 22, 2005

(86) PCT No.: PCT/IN2005/000320
§ 371 (c)(1),
(2), (4) Date: Oct. 16, 2008

(87) PCT Pub. No.: WO2006/033117
PCT Pub. Date: Mar. 30, 2006

(65) Prior Publication Data
US 2009/0093647 A1    Apr. 9, 2009

(30) Foreign Application Priority Data
Sep. 23, 2004   (IN) .............................. 967/CHE/2004

(51) Int. Cl.
*C07C 231/02* (2006.01)
(52) U.S. Cl.
USPC .................. 554/69; 554/35; 554/68; 554/70; 564/143; 564/123; 564/130; 564/137; 564/142
(58) Field of Classification Search
USPC ......................................................... 554/69
See application file for complete search history.

(56) References Cited

U.S. PATENT DOCUMENTS

| | | | |
|---|---|---|---|
| 2,058,013 A | * | 10/1936 | Henke et al. ..................... 554/69 |
| 3,417,114 A | | 12/1968 | Kuceski et al. |
| 3,674,851 A | | 7/1972 | Senoo et al. |
| 3,751,465 A | | 8/1973 | Takahashi et al. |
| 3,856,791 A | | 12/1974 | Daniher et al. |
| 4,034,040 A | * | 7/1977 | Cronin et al. .................. 564/388 |
| 5,206,225 A | | 4/1993 | Horstmann et al. |
| 5,254,684 A | | 10/1993 | Izumi et al. |
| 6,667,341 B2 | | 12/2003 | Lan-Hargest et al. |

FOREIGN PATENT DOCUMENTS

| | | |
|---|---|---|
| GB | 1 521 997 | 8/1978 |
| JP | 03-246265 | * 11/1991 |

OTHER PUBLICATIONS

Ruhoff, J.R. et al., A series of aliphatic dimethyl amides, 1937, Journal of the American Chemical Society, vol. 59, pp. 401-402 (2 pages).*
Lee, W.S. et al., N,N-dimethylaminatio of acid chlorides with DMF, 2000, Synthetic Communications, vol. 30, No. 23, pp. 4241-4245 (5 pages).*
Tatezawa, O. et al., JP 03-246265, English Abstract from PAJ., 1991, (1 page).*
Tatezawa, O. et al., JP 03-246265, English Abstract from CAPLUS, 1991, (1 page).*
JP 03-246265, Tatezawa, O. et al. , Production of Fattya cid Amide, 1991, English translation, pp. 1-16 & cover page.*
Rice, L. et al., Pungents. Fatty acid amides, 1954, Journal of the American Chemical Society, vol. 76, pp. 3730-3731.*
Simon G. Alcock, et al "On the conjugative isomerizations of .beta. ,.gamma.-unsaturated esters. Stereochemical generalizations and predictions for 1,3-prototropic shifts under basic conditions" J. Org. Chem., 1985, 50 (19), pp. 3526-3535; Sep. 1985.
A. C. Cope, et al "N,N-Dimethylcyclohexylmethylamine [Cyclohexanemethylamine, N,N-dimethyl-]" Organic Syntheses, Coll. vol. 4, p. 339 (1963); vol. 39, p. 19 (1959).

* cited by examiner

*Primary Examiner* — Yate K Cutliff
(74) *Attorney, Agent, or Firm* — Workman Nydegger

(57) ABSTRACT

Disclosed herein is a process for producing Dialkyl substituted fatty acids amides. More particularly the present invention provides a process for producing pure form of N,N-dimethylamide of aliphatic carboxylic acids, wherein the aliphatic carboxylic acid is Octanoic Acid and Hexanoic Acid. The disclosed process comprises condensing Alkanoyl Chloride with dilute solution of Dialkylamine at a temperature of about 8 to 12° C. and isolating the crude by salting out the reaction mixture employing Sodium Chloride and distilling the same under vacuum.

21 Claims, No Drawings

PROCESS FOR PRODUCING N,N-DIALKYL SUBSTITUTED FATTY ACIDS AMIDES

FIELD OF THE INVENTION

In general this invention relates to a process for producing Dialkyl substituted fatty acids amides. More particularly, the present invention provides for a process for producing pure form of N,N-Dialkylamides of aliphatic carboxylic acids.

BACKGROUND OF THE INVENTION

Dialkyl substituted fatty acids amides are very useful in the commercial-scale production of personal-care formulations, diluents for pesticides and such formulated products.

Several processes for producing different short chain, long chain fatty acids or mixed fatty acids amides or substituted fatty acids amides are known in the prior art. These processes differ from each other with respect to the different process chemistry employed, use of the different basic raw materials, and different experimental parameters.

British patent GB 1,521,997 to Kreidl, et al., discloses that carboxylic acids can be converted with very good yields into the appropriate N,N-disubstituted carboxylic amides when an adduct formed from a disubstituted formamide and a chlorinating agent, such as Thionyl Chloride, is used as the aminating agent.

U.S. pat. No. 3,417,114 to Kuceski discloses method for producing amides by reacting an ester of a carboxylic acid with an amine, using an alkoxide of an alkali metal as catalyst.

U.S. pat. No. 3,674,851 to Senoo, et al., discloses a process for the preparation of aliphatic tertiary amides, which comprises reacting a fatty acid with an alcohol. Additionally a catalyst may be employed to accelerate the rate of reaction. Also disclosed is that all or part of starting materials remaining un-reacted and/or by-products may be recycled to the starting reaction mixture, thereby enabling the yield of the desired aliphatic tertiary amides to be remarkably improved.

U.S. pat. No. 3,751,465 to Takahashi, et al., discloses a novel process for the preparation of N,N-Dialkyl-substituted fatty amides, which comprises reacting at a temperature in the range of 50 to 1000° C. under pressure a nitrile with an alcohol, with or without employing a catalyst, and recycling at least a part of the by-products of the reaction to the starting reaction mixture.

U.S. pat. No. 3,856,791 to Daniher, et al., discloses a novel method for producing amides by contacting phosgene with a mixture of an organic compound containing at least one active hydrogen atom and an acid salt of an amine.

U.S. pat. No. 5,254,684 to Izumi, et al., discloses a process for producing an amide which comprises subjecting an Oxime to liquid phase rearrangement in the presence of phosphorous pentaoxide and at least one compound selected from the group consisting of N,N-Dialkyl amides, N-alkyl cyclic amides and Dialkyl Sulfoxides and optionally a Fluorine containing strong acid or its derivative. The said process can rearrange an Oxime to a corresponding amide in a good yield under mild reaction conditions in the presence of a less stoichiometric amount of a catalyst.

U.S. pat. No. 5,206,225 to Horstmann, et al., discloses the new use of certain alkyl carboxylic acid dimethylamides for prevention of crystallization during the application of aqueous spray liquors based on specific pesticidally active compounds.

Ruhoff, et al., (JACS, Vol. 59, p 401, 1937) reported a process for producing Dimethyl Amides by heating Acetic Acid saturated with gaseous Dimethyl Amine at 35° C. for 5 hrs to 200° C. in a steel bomb, adding Caustic potash to take up water and Acetic Acid and distilling the purified liquid to obtain Dimethyl Amides. Also reported is a process for obtaining Dimethyl Amides in good yields by adding the Acid Chloride in drops during 3 hrs to a concentrated aqueous solution of three moles of Amine kept at −20 to −10° C., saturating the resulting mixture with KOH in the cold and separating and distilling the Dimethyl Amide.

Organic Syntheses Coll. Vol. 4, p. 339, reports a process for producing N, N-Dimethyl Cyclohexane Carboxamide. Thionyl Chloride [179 g] [1.5 m] is added to Cyclohexane Carboxylic Acid during 5 minutes. The mixture is refluxed in an oil bath for 2 hrs and cooled to room temperature (RT). 200 ml of Benzene is charged and the reaction mixture is distilled out till the vapor temperature reaches 95° C. The same operation is repeated with another 200 ml of Benzene. In another flask, a solution of 135 g of Dimethyl Amine [3.0 m] is charged in 150 ml of Anhydrous Benzene and cooled in an ice bath. The Acid Chloride is added to the mixture during 2 hrs and the mixture is stirred overnight. 200 ml of water is added to the mixture and the separated aqueous layer is re-extracted with ether. The combined organic layer is washed with saturated Nacl solution and dried with Magnesium Sulfate. The organic layer is distilled under vacuum to obtain the pure product 138 g [89%].

Textbook of practical Organic Chemistry, by Vogel, 5$^{th}$ Edition, page 708 has reported method of preparation of amides from acid halides. The reaction of acid chloride with an excess of Ammonia represents one of the best procedures for the preparation of amides. The use of primary amines or secondary amines in place of Ammonia yields corresponding secondary or tertiary amides in reaction with acid chlorides. The method of preparation of Hexanamide is also reported. 125 ml of concentrated Ammonia [d-0.88] [25%] [1.96 m] is placed in an ice bath and Hexanoyl Chloride 56 g [0.42 m] is introduced during 2.0 hrs. The solid is filtered and dried to obtain 30 g of Hexanamide [Yield—63%].

Textbook of practical Organic Chemistry, by Vogel, 5$^{th}$ Edition, page 692 has also reported methods of preparation of Hexanoyl Chloride. 58 g [0.5 m] of Hexanoic Acid is heated on a water bath and 72 g [0.6 m] of Thionyl Chloride is added in 45 minutes. The mixture is refluxed for 30 minutes and the Hexanoyl Chloride is isolated by fractional distillation [B.pt.—150-155° C.]. Yield=56 g [83%].

Also reported is the method of preparation of amides from esters. Amides are easily prepared by the interaction of carboxylic esters with concentrated Aqueous Ammonia [Ammonolysis]. The reaction proceeds readily in cold, particularly when the methyl esters of lower molecular weight carboxylic acids are involved, e.g.—Dimethyl Succinate to Succinamide.

Also reported is the method of preparation of amides from Nitriles. Partial hydrolyses of the Nitriles, [for e.g.—Phenyl Acetamide from Benzyl Cyanide] where the nitrile is dissolved in Conc. Hcl at 40° C. would yield amides.

The present invention discloses an alternative route for producing Dialkyl substituted fatty acid amides, which provide a considerably simple process step to obtain the pure form of N,N-Dialkylamides of aliphatic carboxylic acids wherein the carboxylic acid is Hexanoic Acid or Octanoic Acid.

SUMMARY OF THE INVENTION

It is the principal aspect of the present invention to provide an industrially feasible and concise process for producing a pure form of N,N-dialkylamide of aliphatic carboxylic acids, the process comprising condensing Alkanoyl Chloride with dilute solution of Dimethyl Amine at a temperature of 8 to 12° C. and isolating the crude by salting out the resultant.

It is also an aspect of the present invention to provide for a process for producing a pure form of N,N-Dialkylamides of aliphatic carboxylic acids, wherein the said N,N-dialkylamide is a Dimethylamide of Hexanoic Acid, which is prepared by condensing Hexanoyl Chloride with dilute solution of Dimethyl Amine at a temperature of 8 to 12° C. and isolating the crude by salting out the resultant.

In another aspect of the present invention, there is provided a process for producing a pure form of N,N-Dialkylamide of aliphatic carboxylic acids, wherein the said N,N-Dialkylamide is a Dimethylamide of Octanoic acid, which is prepared by condensing Octanoyl Chloride with the dilute solution of Dimethyl Amine at a temperature of 8 to 12° C. and isolating the crude by salting out the resultant.

In still another aspect of the present invention, there is provided a simple isolation process for obtaining a pure form of N,N-Dialkylamides of aliphatic carboxylic acids, wherein the process comprises adding Sodium Chloride in the reaction mixture which is prepared by condensing Alkanoyl Chloride with dilute solution of Dimethyl Amine and salting out the reaction mixture to get the pure product.

In still another aspect of the present invention, there is provided a process for producing pure form of N,N-dialkylamide of aliphatic carboxylic acids, wherein the process is carried out in liquid medium.

In a preferred embodiment there is provided a process for producing a pure form of Dimethylamide of Octanoic Acid wherein the process comprising, charging diluted aqueous solution of Dimethyl Amine in a reaction pot at room temperature and cooling the same till 10±2° C., adding the Octanoyl Chloride at a temperature of to 8-12° C., stirring the reaction mixture for about 30 minutes and allowing the reaction mixture to attain room temperature and further stirring for about 1 hour, separating the lower aqueous layer and upper organic layer, adding the Sodium Chloride to organic layer and salting out the crude and distilling the same under vacuum to get pure Dimethylamide of Octanoic Acid.

In another preferred embodiment there is provided a process for producing a pure form of Dimethylamide of Hexanoic Acid wherein the process comprises, charging diluted aqueous solution of Dimethyl Amine in a reaction pot at room temperature and cooling the same till 10±2° C., adding the Hexanoyl Chloride at a temperature of about 8-12° C., stirring the reaction mixture for about 30 minutes and allowing the reaction mixture to attain room temperature and further stirring for about 1 hour, adding the Sodium Chloride to the reaction mixture and salting out the crude and distilling the same under vacuum to get pure Dimethylamide of Hexanoic Acid.

DETAILED DESCRIPTION OF THE INVENTION

The present invention relates to a novel and industrially applicable process for producing highly pure form of N,N-Dialkylamides of aliphatic carboxylic acids, which has an advantage from prior art processes in providing a considerable simplification of the process as well as avoiding high temperature and pressure.

According to present invention, the reaction between Acid Chloride and diluted solution of Dimethylamine is carried out at a temperature of 8-12° C. and thus avoids very low temperature as well as very high temperature, as very low temperature would slow down the reaction rate and high temperature would promote side reactions and the formation of by-products.

According to the present invention, the process providing simple isolation of N,N-dialkylamide of aliphatic carboxylic acids by employing Sodium Chloride and salting out to get the crude product, instead of using potassium Hydroxide in cold condition to remove the acid and water as mentioned in the prior art, thus avoiding the additional process step and enabling a more simplified but precise process.

This invention is explained below in more detail, referring to EXAMPLEs, which are described by way of illustration and not by way of limitation:

Example 1

Preparation of Hexanoyl Chloride:

116.2 g of Hexanoic Acid is charged at room temperature and heated to 40° C., then 142.7 g of Thionyl Chloride is added over a period of 1 hour and the reaction mixture is heated to reflux at 90° C. for 1 ½ hour to obtain crude Hexanoyl Chloride.

Example 2

Preparation of Crude Hexanamide:

135.03 g of Dimethyl Amine solution is charged at room temperature and cooled to 10±2° C., then Hexanoyl Chloride obtained in EXAMPLE 1 is charged at 8 to 12° C. over a period of 2 hours, and the reaction mixture is stirred at 10 to 15° C. for 30 minutes and then stirred at room temperature for 1 hour. To this saturated reaction mixture is added 29.80 g of Sodium Chloride, then upper organic layer is separated from lower aqueous layer and 0.994 g of Sodium Sulphate is added to the organic layer to take up water, and the mixture is filtered to obtain crude Hexanamide.

Example 3

Purification of Hexanamide:

Crude Hexanamide obtained in EXAMPLE 2 is distilled under vacuum to obtain pure product (78.31% yield), with GC purity of 99.15%.

Example 4

Preparation of Octanoyl Chloride:

144.2 g of Octanoic Acid is charged at room temperature and heated to 40° C., then 154.64 g of Thionyl Chloride is added over a period of 1 hour and the reaction mixture is heated to reflux at 110° C. for 1½ hour to obtain crude Octanoyl Chloride.

Example 5

Preparation of Crude Octanamide:

135.03 g of Dimethyl Amine solution is charged at room temperature and cooled to 10±2° C., then Octanoyl Chloride obtained in EXAMPLE 4 is charged at 8 to 12° C. over a period of 2 hours, and the reaction mixture is stirred at 10 to 15° C. for 30 minutes and then stirred at room temperature for 1 hour and the upper organic layer is separated from lower aqueous layer and 29.80 g of Sodium Chloride (20% solution) is added to the organic layer. This organic layer is washed and 9.94 g of Sodium Sulphate is added to the organic layer to take up water, and the mixture is filtered to obtain crude Octanamide.

Example 6

Purification of Octanamide:

Crude Octanamide obtained in Example 5, is distilled under vacuum to obtain pure product (82.92% yield), with GC purity of 99.57%.

Certain modifications and improvements of the disclosed invention will occur to those skilled in the art without departing from the scope of invention, which is limited only by the appended claims.

We claim:

1. A process for producing Dialkyl substituted fatty acids amides in an aqueous solution, the process comprising:
    condensing an Alkanoyl Chloride with a dilute aqueous solution of Dialkylamine at a temperature of 8 to 12° C. to produce a crude Dialkyl substituted fatty acid amide product;
    isolating the crude Dialkyl substituted fatty acid amide product from the aqueous media by salting out the reaction mixture employing Sodium Chloride; and
    distilling the crude Dialkyl substituted fatty acid amide product under vacuum to obtain a purified Dialkyl substituted fatty acid product.

2. The process according to claim 1, wherein the Dialkyl substituted fatty acid amide is N,N-dialkylamide of aliphatic carboxylic acids.

3. The process according to claim 2, wherein the N,N-Dialkylamide of aliphatic carboxylic acid is N,N-Dimethylamide of Hexanoic Acid.

4. The process according to claim 2, wherein the N,N-Dialkylamide of aliphatic carboxylic acid is N,N-Dimethylamide of Octanoic Acid.

5. The process according to claim 1, wherein the Alkanoyl chloride is Hexanoyl Chloride.

6. The process according to claim 1, wherein the Alkanoyl chloride is Octanoyl Chloride.

7. The process according to claim 1, wherein the Dialkylamine is Dimethyl Amine.

8. The process according to claim 1, wherein the process is carried out in a liquid medium.

9. A process for producing Dialkyl substituted fatty acids amides in aqueous solution, the process comprising:
    charging a dilute aqueous solution of Dialkylamine in a reaction pot at room temperature and cooling the aqueous solution of Dialkylamine,
    adding an Alkanoyl Chloride to the reaction pot at a temperature of 8-12° C.,
    stirring the reaction mixture for about 30 minutes,
    allowing the reaction mixture to attain room temperature, further stirring for about 1 hour,
    separating an organic layer from an aqueous layer,
    adding Sodium Chloride to organic layer,
    salting out a crude Dialkyl substituted fatty acid amide product, and
    distilling the crude Dialkyl substituted fatty acid amide product under vacuum to obtain a purified Dialkyl substituted fatty acid product.

10. The process according to claim 9, wherein the dilute aqueous solution of Dialkylamine is cooled to a temperature of 10±2° C.

11. The process according to claim 9, wherein the Dialkyl substituted fatty acid amide is N,N-Dialkylamide of aliphatic carboxylic acids.

12. The process according to claim 11, wherein the N,N-Dialkylamide of aliphatic carboxylic acid is N,N-Dimethylamide of Octanoic Acid.

13. The process according to claim 9, wherein the Alkanoyl chloride is Octanoyl Chloride.

14. The process according to claim 9, wherein the Dialkylamine is Dimethyl Amine.

15. A process for producing Dialkyl substituted fatty acids amides in aqueous solution, the process comprising:
    charging a dilute aqueous solution of Dialkylamine in a reaction pot at room temperature,
    cooling the dilute aqueous solution of Dialkylamine,
    adding an Alkanoyl Chloride to the reaction pot at a temperature of 8-12° C. over a period of 2 hours to form a reaction mixture,
    stirring the reaction mixture for about 30 minutes a temperature of 10-15° C.,
    allowing the reaction mixture to attain room temperature, further stirring for about 1 hour,
    adding Sodium Chloride to the reaction mixture,
    salting out a crude Dialkyl substituted fatty acid amide product, and
    distilling the crude Dialkyl substituted fatty acid amide product under vacuum to obtain a purified Dialkyl substituted fatty acid product.

16. The process according to claim 15, wherein the dilute aqueous solution of Dialkylamine is cooled to a temperature of 10±2° C.

17. The process according to claim 15, wherein the Dialkyl substituted fatty acid amide is N,N-dialkylamide of aliphatic carboxylic acids.

18. The process according to claim 17, wherein the N,N-Dialkylamide of aliphatic carboxylic acid is N,N-Dimethylamide of Hexanoic Acid.

19. The process according to claim 15, wherein the Alkanoyl chloride is Hexanoyl Chloride.

20. The process according to claim 15, wherein the Dialkyl amine is Dimethyl Amine.

21. The process of claim 1, wherein the step of isolating the crude dialkyl substituted fatty acid amide product from the aqueous media is carried out at a temperature that is greater than the temperature used to produce the crude dialkyl substituted fatty acid amide product.

* * * * *